United States Patent [19]

Holtkamp, Sr.

[11] Patent Number: Plant 7,006

[45] Date of Patent: Aug. 29, 1989

[54] AFRICAN VIOLET PLANT NAMED DOLLY

[76] Inventor: Reinhold Holtkamp, Sr., Werther Strasse 112, D4294 Isselburg, Fed. Rep. of Germany

[21] Appl. No.: 251,248

[22] Filed: Sep. 30, 1988

[51] Int. Cl.[4] ..... A01H 5/00
[52] U.S. Cl. ..... Plt./69
[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of African violet named Dolly characterized by its single, variegated flowers with a white background and a purplish blue frilled edge that is larger on the 2 small petals than on the 3 big petals; strong, upright flower stems that curve slightly toward the center to form a compact bouquet above the leaves; medium green velvety leaves, profuse flowering, vigorous growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Dolly.

The new cultivar was referred to during the breeding and selection process by the designation G 12/54 and is a product of a planned breeding program. The new cultivar was originated from a cross made by me in the controlled breeding program in Haffen, Federal Republic of Germany. The female, or seed parent was a cultivar designated XIX 4158. The male, or pollen parent was a cultivar designated 67.

Dolly was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Dolly has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Dolly, which in combination distinguish this African violet as a new and distinct cultivar:

(1) Strong, upright flower stems curving slightly toward the center.
(2) Single, variegated flowers with white background and purplish blue frilled edges.
(3) Profuse flowering.
(4) Each plant carries 8–10 and more upright flower stems each of which carries 8–10 and more flowers.
(5) Long lasting, non-dropping flowers.
(6) Vigorous grower.
(7) Plant saleable 10 to 11 weeks after potting.
(8) Seed capsules push slightly through.
(9) Medium green velvety and shiny leaves.

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 2 p.m. in Nahsville, Tenn.

Botanical classification: *Saintpaulia ionantha,* Ramat., c.v. Dolly.

Parentage:

*Male parent.*—67.

*Female parent.*—XIX 4158.

Propagation: The new cultivar holds its distinguishing characteristics through successive propagations by leaf cuttings.

Plant: From 9 to 11 cm tall when grown in pots, and approximately 24–26 cm in diameter when fully grown.

*Leaves.*—General form: Oval to heart-shaped. Diameter 65–75 mm wide and 75–85 mm long. Texture: Velvety. Aspect: Hairy, slightly shiny. Veins: Upperside: visible, underside: well pronounced, light green, shiny. Color (upperside): Yellow-Green Group 147 between A and B. Color (underside): Yellow-Green Group 148 D. Petiole: Strong upright, light green, hairy.

*Flowers.* Buds: Ball-shaped, 7–9 mm just before opening. Sepals: Five (5). Color: Green. Calyx: Shape: Funnel-shaped. Aspect: Spear-shaped, hairy. Peduncle: Character: Strong upright, hairy. Color: Green with purplish touch. Individual flowers: Size: 45–50 mm. Shape: Single violet-shaped (3 large and 2 small petals), frilled edges. Color (upperside): White with edges being Violet Group 87 between A and B. Under cooler temperature and more intensive lighting, the color of the edges tends to intensify. Color (underside): White with edges being Violet Group 87. Borne: Each flower stem carries 8–10 and more flowers on strong, upright peduncles that are free standing above the leaves, thereby forming a compact bouquet. Flowering habit: Flowers 10–11 weeks after potting.

*Reproductive Organs.*—Stamens: Two (2). Anthers: 2 composed of 4 anther cells, seed capsule pushes slightly through. Filaments: Yellowish green, 5 mm long. Pollen Color: Yellow Group 7 A. Styles: 7 mm long, purplish blue, base of ovary light green and hairy.

*Roots.*—Normally developed, white when young, turning slightly brownish when older.

Disease resistance: Good.

General observations: Dolly is a very attractive, vigorous grower with velvety medium green leaves. A tight bouquet of single violet-shaped flowers free standing above the leaves develops after approximately 10–11 weeks. Each of the 8–10 and more strong flower stems carries 8–10 and more variegated flowers having a white background and purplish blue frilled edges. On the 2 small petals, the purplish blue edge is approximately 4 mm wide, on the 3 big petals it can be as thin as ½ mm. The flowers are long-lasting and non-dropping and the seed capsules push slightly through.

I claim:

1. A new and distinct cultivar of African violet named Dolly, as described and illustrated, and particularly characterized by its single, variegated flowers with a white background and a purplish blue frilled edge that is larger on the 2 small petals than on the 3 big petals; strong, upright flower stems that curve slightly toward the center to form a compact bouquet above the leaves; medium green velvety leaves, profuse flowering, vigorous growth habit, flowering 10–11 weeks after potting, and its long lasting and non-dropping flowers.

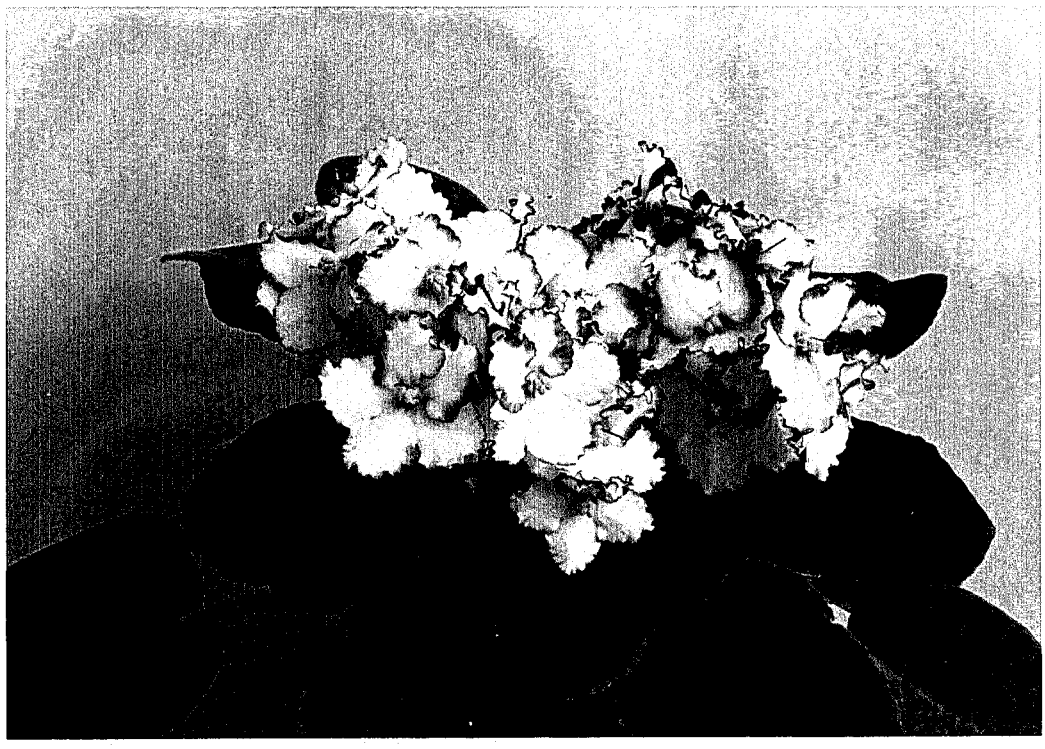

* * * * *